United States Patent [19]

Shipko et al.

[11] Patent Number: 5,697,936
[45] Date of Patent: Dec. 16, 1997

[54] DEVICE FOR REMOVING AN ELONGATED STRUCTURE IMPLANTED IN BIOLOGICAL TISSUE

[75] Inventors: Frederick J. Shipko, Spring Church; Chun Kee Lui, Monroeville, both of Pa.

[73] Assignee: Cook Pacemaker Corporation, Leechburg, Pa.

[21] Appl. No.: 433,820

[22] Filed: May 4, 1995

Related U.S. Application Data

[63] Continuation-in-part of Ser. No. 255,602, Jun. 8, 1994, Pat. No. 5,507,751, which is a continuation-in-part of Ser. No. 42,375, Apr. 2, 1993, Pat. No. 5,632,749, which is a division of Ser. No. 691,706, Apr. 26, 1991, Pat. No. 5,207,683, which is a continuation-in-part of Ser. No. 363,960, Jun. 9, 1989, Pat. No. 4,943,289, which is a continuation-in-part of Ser. No. 347,217, May 3, 1989, Pat. No. 5,011,482, which is a continuation-in-part of Ser. No. 298,100, Jan. 17, 1989, Pat. No. 5,013,310, which is a continuation-in-part of Ser. No. 269,711, Nov. 10, 1988, Pat. No. 4,939,069.

[51] Int. Cl.$^6$ ................................................. A61B 17/50
[52] U.S. Cl. ................................................ 606/108; 128/639
[58] Field of Search ................................ 606/108, 110; 607/116, 126, 127, 128, 130, 131; 128/897, 639; 604/93

[56] References Cited

U.S. PATENT DOCUMENTS

| 3,118,159 | 1/1964 | Kollmann | 15/104.33 |
| 3,243,755 | 3/1966 | Johnston | 128/841 |
| 3,516,412 | 6/1970 | Ackerman | 128/419 P |
| 3,757,375 | 9/1973 | Strom | 15/104.33 |
| 3,841,308 | 10/1974 | Tate | 128/772 |

(List continued on next page.)

FOREIGN PATENT DOCUMENTS

| 2558376 | 7/1985 | France | 128/785 |
| 3532653 | 3/1987 | Germany | 128/344 |
| 8807390 | 10/1988 | Japan | 128/785 |
| 1277107 | 6/1972 | United Kingdom | 128/785 |

OTHER PUBLICATIONS

"Pacemaker Electrode Explantation Set," William Cook Europe A/S, Date Unknown.

Meibom, "A New Method for Transvenous Lead Explanation," 3rd European Symposium on Cardiac Pacing, Torremolinos, Malaga, Spain, *PACE*, vol. 8, May–Jun. 1985, Part II, Abstract 215, p.A–54.

(List continued on next page.)

*Primary Examiner*—William E. Kamm
*Assistant Examiner*—Kennedy J. Schaetzle
*Attorney, Agent, or Firm*—Richard J. Godlewski

[57] ABSTRACT

A device (10) for removing from a patient (12) a previously implanted elongated structure (14), such as a catheter, sheath, defibrillator lead, pacemaker lead (15) or the like. The device (10) includes a snare (24) which encircles and reversibly grasps either the proximal end (16) or the distal end (20) of the elongated structure (14), as well as a sheath member (22) for delivering the snare (24) to the particular end (16 or 20) of the structure (14) to be grasped. The device (10) is thereby capable of performing two different functions in removing the elongated structure (15); when employed to grasp the proximal end (16) of the elongated structure (14), the device (10) serves to fix the position of the structure (14) thereby allow a separate coring cannula or sheath to advance along the structure (14) and separate it from any tissue which has encapsulated it; while alternatively the sheath member (22) may itself be or include a coring or dilator sheath (36), and the snare (24) employed to grasp the distal end (20) of the elongated structure (14) after the structure (14) is freed by the coring or dilator sheath (36) from any tissue which has encapsulated it. A special advantage of the device (10) of the present invention over the prior art is that the grasping of the structure end (16 or 20) by the snare (24) is reversible; this is of particular value when the removal procedure must be interrupted.

22 Claims, 4 Drawing Sheets

U.S. PATENT DOCUMENTS

| | | | |
|---|---|---|---|
| 3,906,938 | 9/1975 | Fleischhacker | 128/772 |
| 4,000,745 | 1/1977 | Goldberg | 128/419 P |
| 4,040,413 | 8/1977 | Ohshiro | 128/6 |
| 4,466,690 | 8/1984 | Osypka | 128/419 P |
| 4,471,777 | 9/1984 | McCorkle, Jr. | 128/303 R |
| 4,498,482 | 2/1985 | Williams | 128/786 |
| 4,541,681 | 9/1985 | Dorman et al. | 339/100 |
| 4,574,800 | 3/1986 | Peers-Trevarton | 128/785 |
| 4,576,162 | 3/1986 | McCorkle | 128/303 R |
| 4,582,056 | 4/1986 | McCorkle | 128/303 R |
| 4,706,671 | 11/1987 | Weinrib | 128/341 |
| 4,732,154 | 3/1988 | Shiber | 606/108 |
| 4,762,128 | 8/1988 | Rosenbluth | 604/96 |
| 4,762,130 | 8/1988 | Fogarty et al. | 604/96 |
| 4,773,432 | 9/1988 | Rydell | 128/772 |
| 4,791,939 | 12/1988 | Maillard | 128/419 P |
| 4,796,642 | 1/1989 | Harris | 128/772 |
| 4,834,090 | 5/1989 | Moore | 128/303 R |
| 4,848,342 | 7/1989 | Kaltenbach | 604/104 |
| 4,886,496 | 12/1989 | Conoscenti et al. | 604/96 |
| 4,886,500 | 12/1989 | Lazarus | 128/772 |
| 5,061,257 | 10/1991 | Martinez et al. | 604/282 |
| 5,067,489 | 11/1991 | Lind | 128/772 |
| 5,098,374 | 3/1992 | Othel-Jacobsen et al. | 606/108 |
| 5,098,440 | 3/1992 | Hillstead | 606/108 |
| 5,108,368 | 4/1992 | Hammerslag et al. | 128/772 |
| 5,190,528 | 3/1993 | Fonger et al. | 604/171 |
| 5,231,996 | 8/1993 | Bardy et al. | 128/785 |
| 5,234,437 | 8/1993 | Sepetka | 606/108 |
| 5,342,371 | 8/1994 | Welter et al. | 606/108 |
| 5,387,219 | 2/1995 | Rappe | 606/108 |
| 5,549,615 | 8/1996 | Hocherl et al. | 607/127 |

OTHER PUBLICATIONS

Meibom, "A New Method for Transvenous Lead Explantation," Publisher (if any) and date of Publication Presently Unknown.

Meibom et al., "A New Method for Removal of Embedded Endocardial Electrodes," First Asian–Pacific Symposium, *PACE*, vol. 3, May–Jun. 1980, Abstract No. 77, p. 380.

"Dotter Intravascular Retriever Set and Components," *Cook® Diagnostic and Interventional Products for Radiology, Cardiology and Surgery, Intravascular Retrieval,* 1986, p. 3.

"Wilson–Cook Grasping Forceps," *Wilson–Cook Medical, Inc., Products for Gastroenterology, Endoscopy and Surgery,* 1986–87 Catalog, p. 41.

"Loop Retrievers," *Cook Urological®, Urological Surgical Products, Stone Extractors and Retrievers,* 1986, p. 9.

"Boren–McKinney Retriever Set," *Cook Urological®, Urological Surgical Products, Stone Extractors and Retrievers,* 1986, p. 9.

"Curry Intravascular Retriever Sets and Components," *Cook® Diagnostic and Interventional Products for Radiology, Cardiology and Surgery, Intravascular Retrieval,* 1986, p. 2.

"Grasping Forceps," *Cook Urological®, Urological Surgical Products, Stone Extractors and Retrievers,* 1986, p. 8.

Alt et al., "Entfernung von drei infizierten Elektroden mit Hilfe eines neuen Extraktionsstiletts: Ein Fallbericht," *Herzschr Elektrophys,* vol. 2, 1991, pp. 29–34.

Alt et al., "Removal of Three Implanted Pacing Leads by Means of a New Extraction Stylet," translation of German reference *Herzschr Elektrophys,* vol. 2, 1991, pp. 29–34.

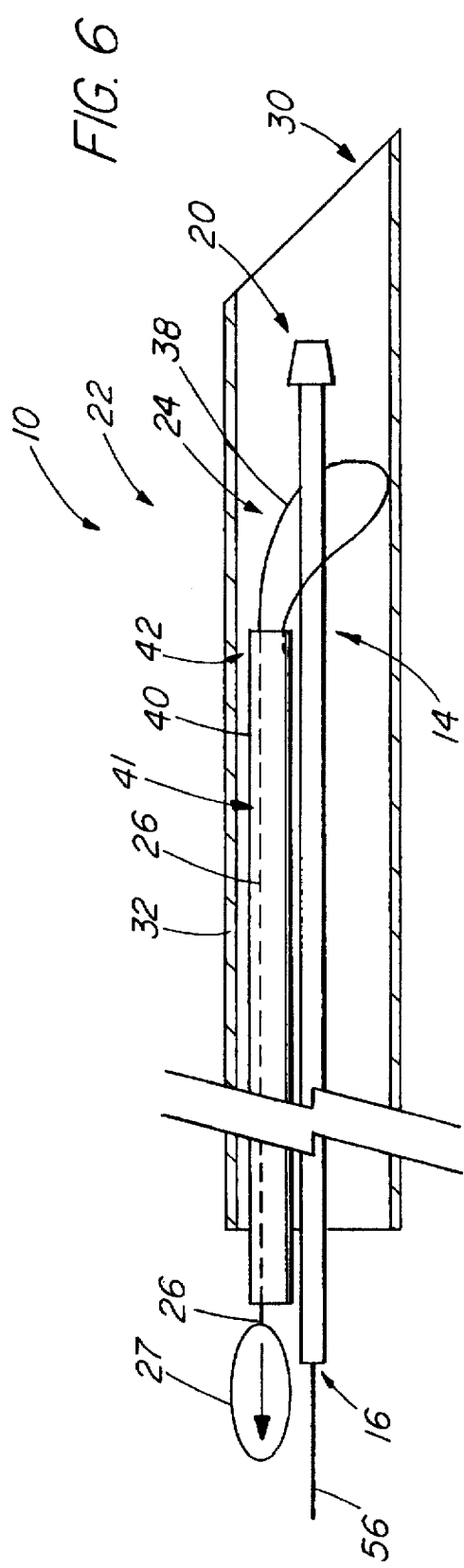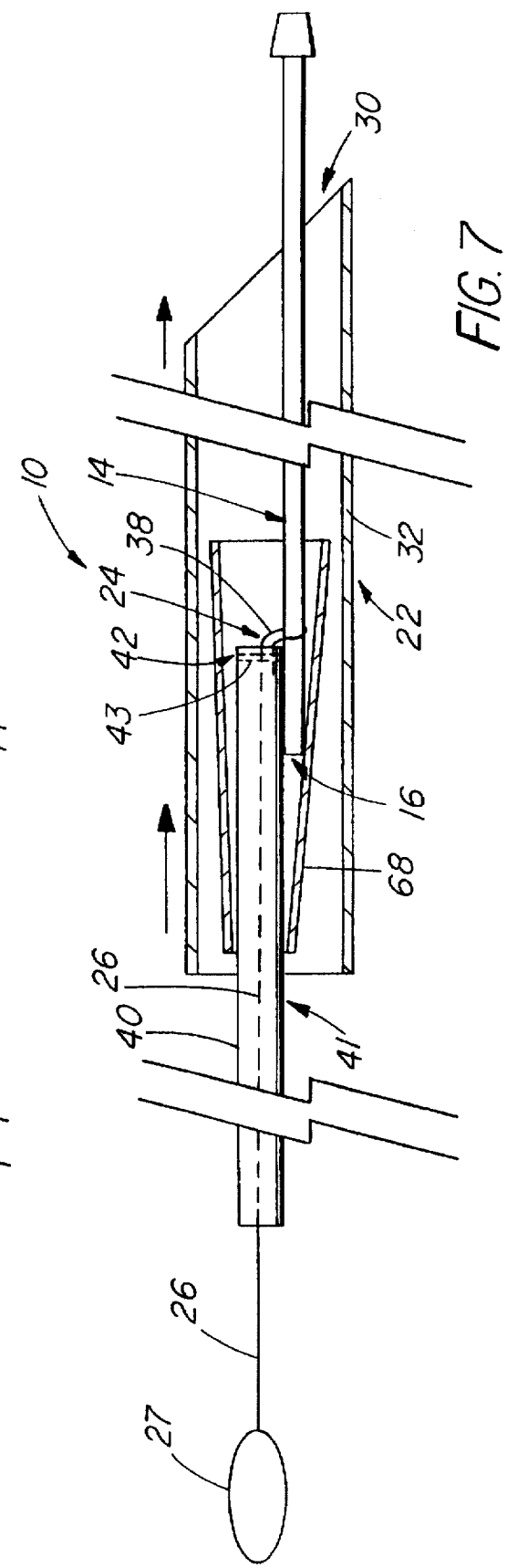

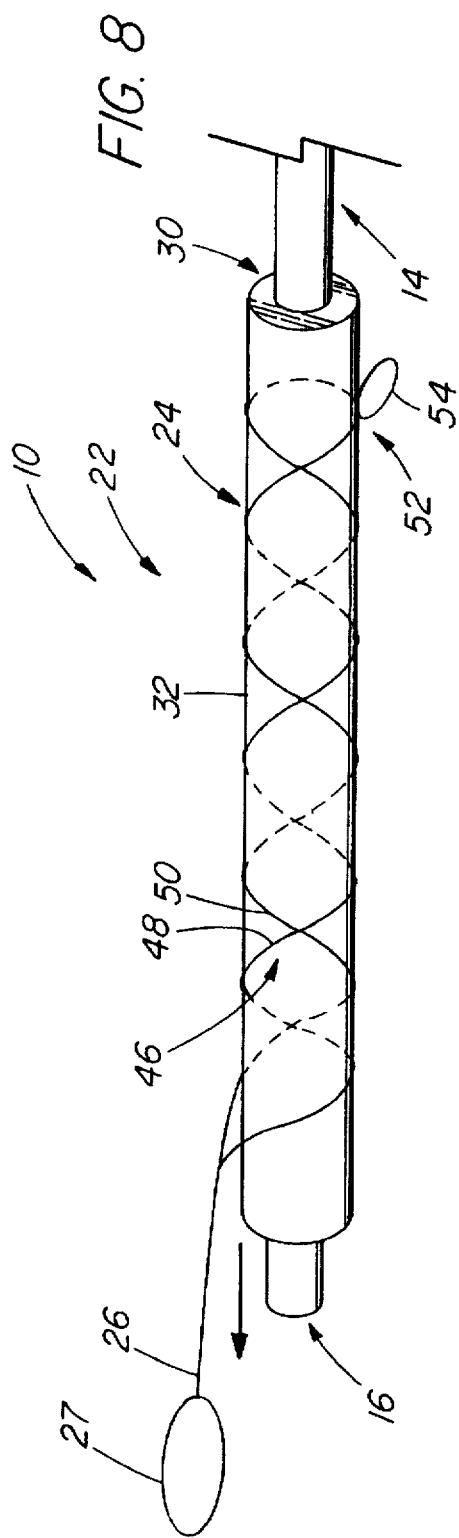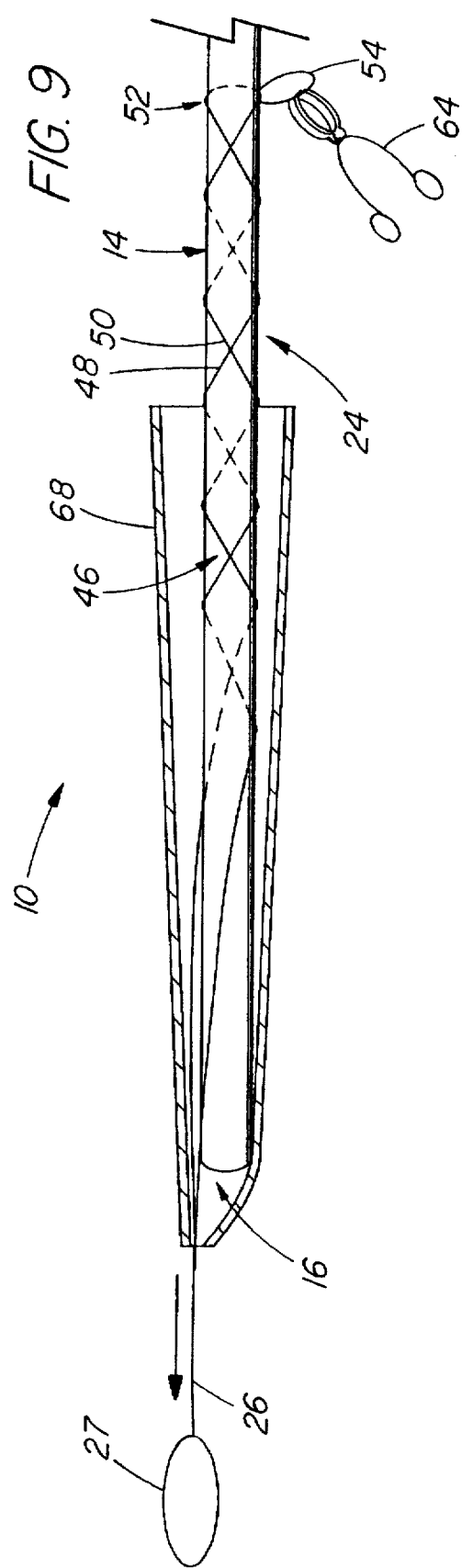

DEVICE FOR REMOVING AN ELONGATED STRUCTURE IMPLANTED IN BIOLOGICAL TISSUE

CROSS-REFERENCE TO RELATED APPLICATIONS

This application is a continuation-in-part of application Ser. No. 08/255,602, filed Jun. 8, 1994, entitled "Locally Flexible Dilator Sheath", now U.S. Pat. No. 5,507,751; which was in turn a continuation-in-part of then-pending application Ser. No. 08/042,375, filed Apr. 2, 1993, entitled "Apparatus for Removing an Elongated Structure Implanted in Biological Tissue", now U.S. Pat. No. 5,632,749; which was a divisional of then-pending application Ser. No. 07/691,706, filed Apr. 26, 1991, now U.S. Pat. No. 5,207,683, entitled "Apparatus for Removing an Elongated Structure Implanted in Biological Tissue"; which was a continuation-in-part of then-pending application Ser. No. 07/363,960, filed Jun. 9, 1989, now U.S. Pat. No. 4,943,289, entitled "Apparatus for Removing an Elongated Structure Implanted in Biological Tissue"; which was a continuation-in-part of then-pending application Ser. No. 07/347,217, filed May 3, 1989, now U.S. Pat. No. 5,011,482, entitled "Apparatus for Removing an Elongated Structure Implanted in Biological Tissue"; which was a continuation-in-part of then-pending application Ser. No. 07/298,100, filed Jan. 17, 1989, now U.S. Pat. No. 5,013,310, entitled "Method and Apparatus for Removing an Implanted Pacemaker Lead"; which was a continuation-in-part of then-pending application Ser. No. 07/269,711, filed Nov. 10, 1988, now U.S. Pat. No. 4,939,069, entitled "Method and Apparatus for Separating a Coiled Structure from Biological Tissue." All of the aforementioned applications and issued patents are incorporated herein by reference.

TECHNICAL FIELD

This invention relates generally to surgical devices, and more particularly to a device for separating encapsulating biological tissue from an implanted elongated structure (for example, an implanted cardiac electrical lead such as a pacemaker or defibrillator lead), and/or for removing such an elongated structure from a patient.

BACKGROUND OF THE INVENTION

A variety of medical treatments and surgical methods entail implanting an elongated structure in the body of a human or veterinary patient. Examples of such elongated structures include catheters, sheaths and cardiac electrical leads (such as pacemaker leads and defibrillator leads), and a variety of other devices. Over time, it may become necessary or desirable to remove such an elongated structure from the body of the patient. However, problems may be encountered in attempting removal of an elongated structure implanted in biological tissue.

For example, a heart pacemaker is typically implanted in a subcutaneous tissue pocket in the chest wall of a patient, and a pacemaker lead positioned in the vascular system of the patient, extending from the pacemaker and through a vein into a chamber of the patient's heart. The pacemaker lead commonly includes a coiled structure such as an electrical wire coil for conducting electrical signals (such as stimulating and/or sensing signals) between the pacemaker and the heart. Defibrillator leads are generally similar and, like pacemaker leads, are located about the heart, but are affixed both internally and externally of the heart. A typical lead includes one or more coaxial or lateral helical wire coils having a hollow inner passageway that extends the entire length of the wire coil or coils. The wire coils are surrounded by an electrically insulating material such as a flexible tube, sheath or coating. The insulating material may be silicone or polyurethane, and serve simultaneously to protect the wire coils from body fluids and to insulate the wire coils from one another.

While cardiac electrical leads typically have a useful life of many years, over time pacemaker and defibrillator leads unfortunately become encapsulated by fibrotic tissue against the heart itself or the wall of the vein, or against other surrounding tissue. Encapsulation is especially encountered in areas where the velocity of the flow of blood is low. The fibrotic tissue is tough and makes it difficult to remove the lead from the area of the heart without causing trauma to the area. For example, when small diameter veins through which a pacemaker lead passes become occluded with fibrotic tissue, separating the lead from the vein can cause severe damage to the vein such as dissection or perforation of the vein. Furthermore, separation of the lead from the vein is usually not possible without restricting or containing movement of the lead, that is, fixing the lead in position with respect to the patient, in particular, with respect to the patient's vein.

To avoid this and other possible complications, some useless pacemaker or other leads are simply left in the patient when the pacemaker or defibrillator is removed or replaced. However, such a practice can incur the risk of an undetected lead thrombosis, which can result in stroke, heart attack, or pulmonary embolism. Such a practice can also impair heart function, as plural leads can restrict the heart valves through which they pass.

There are of course many other reasons why removal of a useless lead is desirable. For example, if there are too many leads positioned in a vein, the vein can be obliterated. Multiple leads may be incompatible with one another, interfering with the pacing or defibrillating function. Of course, an inoperative lead can migrate during introduction of an adjacent second lead, and mechanically induce ventricular arrhythmia. Other potentially life-threatening complications can require the removal of the lead as well. For example, removal of an infected pacemaker lead is desirable, so as to avoid septicemia or endocarditis.

Surgical removal of a heart lead in such circumstances often involves open heart surgery, with its accompanying risks, complications and significant costs. A variety of successful methods and apparatus have been devised as alternatives to open heart surgery for heart lead removal. Each alternative has its own usefulness and drawbacks, however.

For example, one method of transvenously extracting a cardiac lead is by the use of a lead removal tool that can be positioned inside the coiled wire of the lead. The lead removal tool includes a wire stylet which engages the coil and locks to it. For convenience, this type of lead removal tool will hereinafter be referred to as a "locking stylet." The second through seventh patent applications and patents cross-referenced above are directed to locking stylets of this type.

One drawback to the use of such a locking stylet is that some leads have obstructions across their internal hollow passages. As a result, the locking stylet cannot be inserted all the way to the distal end of the lead. Distortion of the lead and its coils can pose a similar problem. Of course, some leads (particularly commercially available defibrillator leads) have a solid structure, with no hollow inner passage, so that locking stylets are not applicable with such leads.

Another method of transvenously removing a cardiac lead is simply to withdraw it manually, without the aid of any tool at all. Such a method is possible only when the lead has not been encapsulated in, or restricted by, a blood vessel. However, this method has several drawbacks even in the absence of encapsulation. For example, if the polyurethane or silicone insulation surrounding the wire coil or coils has been damaged, the insulation can sever or separate, and can permit the coiled structure of the lead to unwind and possibly damage the heart and surrounding blood vessels. Surgical removal will then be required. Moreover, most pacemaker leads typically include tines or a corkscrew shape at their tips, or include a conical tip, for securing the distal end of the lead to the wall of a heart cavity. If fibrotic tissue has encapsulated the lead tip, unaided manual extraction of the lead may cause an inward extension or inversion of the heart wall, or may cause permanent damage to the heart, such as tearing a hole in the heart wall.

Yet another method of transvenously extracting a cardiac lead is by the use of a grasping device, such as a forceps or basket that is positionable around the outer surface of a lead or fragments of a lead. One limitation of the use of forceps or a basket for lead withdrawal is that the lead should first be freed from any encapsulating material surrounding it. Another limitation with such use of forceps or a basket is that the forceps or basket grasps the lead only at or adjacent its proximal or free end, and only along a very short portion of that end. The lead, however, may fracture during withdrawal, requiring several attempts to grasp and withdraw the plural fragments of the lead. Moreover, the combined profile of the lead and an encircling basket is relatively large, and has the potential to traumatize tissue during removal. This problem is compounded when the lead extends radially outwardly from the basket against the blood vessel wall, as is often likely, so that the blood vessel may be injured during withdrawal of the lead.

Pacemaker leads can also be removed from the vein of a patient by use of a dilator sheath. Commonly, two coaxial dilator sheaths are positioned over the lead and advanced along the lead so as to loosen the lead from the fibrotic tissue attaching it to the vein wall. Some dilator sheaths are formed from metal and include a sharp leading edge for encountering and severing fibrotic tissue; such sheaths are relatively inflexible and resist bending around natural anatomical curvatures, which can injure or obliterate the vein when advanced towards the distal end of the lead. Other dilator sheaths are formed from flexible plastic tubes, which bend around the natural anatomical curvatures of the vascular system. Unfortunately, the leading edge of such sheaths is often weak, and can buckle during use before the lead is fully loosened from the fibrotic tissue. The parent case, U.S. patent application Ser. No. 08/255,602, discloses a locally and laterally flexible dilator sheath of a rigid material, which functions quite well to sever a cardiac lead from even extremely tough or tenacious encapsulating tissue. The parent case does not disclose any specific portion of the sheath which would engage and allow removal of the distal end of the lead if the distal lead end becomes separated from the remainder of the lead.

SUMMARY OF THE INVENTION

The foregoing problems are solved and a technical advance is achieved in an illustrative device for removing from a patient a previously implanted elongated structure, such as a catheter, sheath, pacemaker lead, defibrillator lead or the like. The device includes a snare which encircles and reversibly grasps either the proximal or the distal end of the elongated structure, as well as a sheath member for delivering the snare to the end of the structure to be grasped.

The device is thereby capable of performing two different functions in removing the elongated structure. When employed to grasp the proximal end of the elongated structure, the device serves to fix the position of the structure, and thereby allow a separate coring cannula or sheath (distinct from the sheath member) to advance along the structure and separate it from any tissue which has encapsulated it. Alternatively, the sheath member may itself be or include a coring or dilator sheath, and the snare of the device is then employed to grasp the distal end of the elongated structure after the sheath has separated the elongated structure from any tissue which has encapsulated it.

A special advantage of the device of the present invention over the prior art is that the grasping of the structure end by the snare is reversible; this is of particular importance when the removal procedure must be interrupted for any of a variety of known reasons. Another advantage of the device of the present invention is its relatively small profile, usually no larger than the diameter of a conventional coring or dilator sheath.

In a first aspect, then, the present invention is directed to a device for removing from a patient a previously implanted elongated structure, the structure having an outside dimension, a free proximal end located either inside or outside the patient, and a distal end normally fixedly located within the patient. The device comprises, in combination, a sheath member having an inside dimension greater than the outside dimension of the elongated structure, and a reversibly collapsible snare associated with the sheath member. The snare is dimensioned to encircle one of the proximal end and the distal end of the elongated structure, and the sheath member delivers the snare to that same one of the proximal and distal end of the elongated structure.

The sheath member can be a single sheath, or two or more parallel or coaxial sheaths. Particularly when the sheath member is a single sheath, the snare can be positioned either within or about the sheath member, preferably affixed to the distal end of the sheath member. The sheath member can alternatively comprise first and second coaxial sheaths, and the snare positioned between them.

It is particularly preferred that the sheath member be (if a single sheath) or include (if two or more sheaths) a locally flexible dilator sheath in accordance with the teachings of the parent patent application, U.S. Ser. No. 08/255,602, cross-referenced above and expressly incorporated by reference herein. It is also preferred that, when the snare is employed to grasp the distal end of the elongated structure, the device of the present invention is used in combination with a locking stylet engaged with the elongated structure. Particularly preferred for this purpose are the locking stylets disclosed in the second through seventh patent applications and patents cross-referenced above, expressly incorporated by reference herein.

Preferred shapes for the reversibly collapsible snare include a wire coil, loop or cylindrical cage, as well as a coiled leaf spring.

The device can also comprise draw means associated with the sheath member and preferably contained within the sheath member, connected to the snare and extending outwardly of the patient. The draw means is moveable in a first direction so as to collapse the snare about the encircled one of the proximal and distal ends of the elongated structure, and is sufficiently rigid to expand the snare and release it from the elongated structure when the draw means is moved in a direction to the first direction. When the snare engages the proximal end of the lead, a tapered outer sleeve is further included with the device to advantageously maintain engagement of an untensioned snare with the lead.

In a second aspect, the present invention is directed to a device of the type disclosed above, comprising a number of the distinct elements described above.

In a third aspect, the present invention is directed to a device of the type disclosed above, specifically adapted for removing an implanted cardiac defibrillator or pacemaker lead from a location about the heart of a patient.

In a final aspect, the present invention is directed to a device of the type disclosed above, specifically adapted for removing an implanted cardiac pacemaker lead from the vascular system of a patient.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which:

FIG. 6 is a cross-sectional view of another preferred embodiment of the present invention;

FIG. 7 is a cross-sectional view of another preferred embodiment of the present invention; and FIGS. 8 and 9 are cross-sectional views of another preferred embodiment of the present invention.

DETAILED DESCRIPTION

Figure 1:
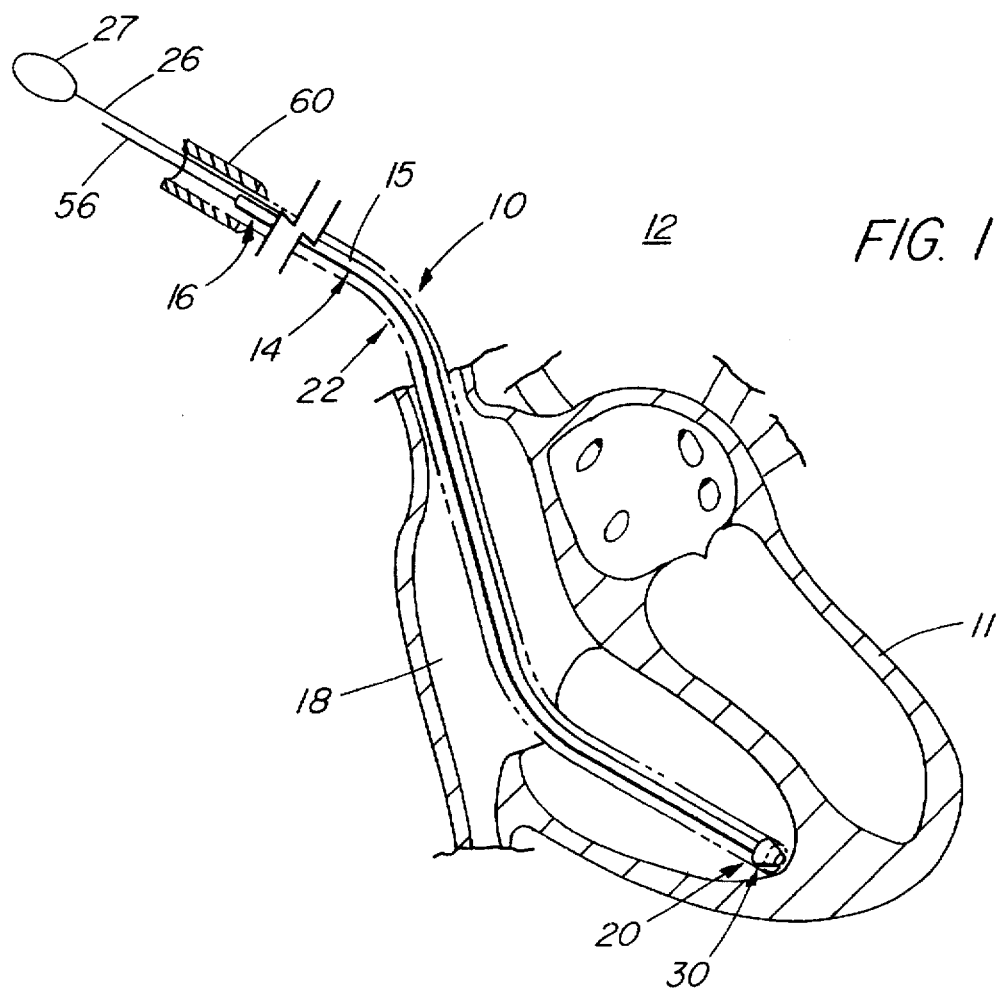
FIG. 1 is a cross-sectional view showing the first preferred embodiment of the present invention during use.
Figure 2:
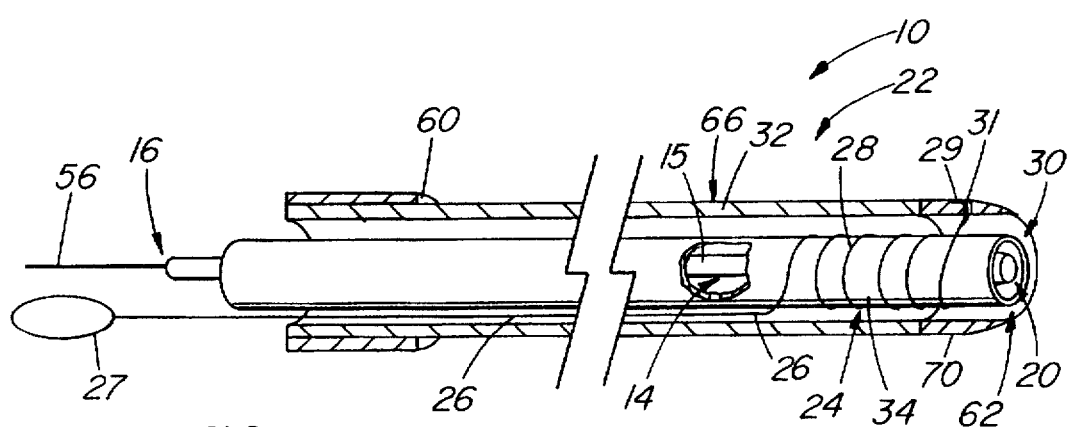
FIG. 2 is another cross-sectional view of the first preferred embodiment of the present invention.

With reference first to FIGS. 1 and 2, a device 10 for removing or extracting a previously implanted elongated structure 14 from a patient 12 is thereshown, and first comprises in combination a sheath member 22 and a reversibly collapsible snare 24 associated with the sheath member 22. The elongated structure 14 is illustrated as a cardiac pacemaker lead 15; while the device 10 of the present invention is particularly useful for removing pacemaker leads 15, it is also useful for removing other implanted, elongated bodies. Such bodies can be defibrillator leads or other cardiac electrical leads, catheters, sheaths, cannulae or the like.

The elongated structure 14 has an outside dimension or diameter, a proximal end 16 located outside at least the vascular system 18 of the patient 12 and preferably positionable outside the patient 12, and a distal end 20 located within the patient. For example, when the elongated structure 14 is the cardiac pacemaker lead 15, the distal end 20 will be located within the vascular system 18 of the patient, and in particular, within a chamber of the patient's heart 11 (such as in an atrium or ventricle of the heart 11). Alternatively, when the elongated structure 14 is a defibrillator lead, the distal end 20 will be located either in or about the heart 11 of the patient 12. The distal ends of other types of elongated structures 14 may not be and need not be near the heart at all; the device 10 will still be useful for removing them.

The sheath member 22 has an inside dimension or diameter greater than the outside dimension or diameter of the elongated structure 14, such that the sheath member 22 can be fit over the proximal end 16 of the structure 14. In the embodiment shown in FIGS. 1 and 2, this permits the sheath member 22 to slide over the elongated structure 14 and sever or assist severing of the structure 14 from any tissue encapsulating it in the patient 12, for example, in the vascular system 18 of the patient.

The reversibly collapsible snare 24 is dimensioned to encircle one of the proximal end 16 and the distal end 20 of the elongated structure 14. In the preferred embodiment shown in FIGS. 1 and 2, the snare 24 is particularly adapted to encircle the distal end 20 of the structure 14, and is carried by the sheath member 22 (for example, affixed to the distal end 30 of the sheath member 22) so that the sheath member 22 delivers the snare 24 to the distal end 20 of the elongated structure 14. When the snare 24 is collapsed about the distal end 20 of the structure 14, it allows the structure 14 to be withdrawn from the patient 12 without risk of severing or fracture. In other preferred embodiments, such as those shown in FIGS. 7 through 9 and described further below, the snare 24 is particularly adapted to encircle the proximal end 16 of the elongated structure 14, so as to fix the position of the structure 14 with respect to the patient 12, and facilitate severing of any encapsulating tissue either by the sheath member 22 or by a different coring cannula or dilator sheath (not shown).

While the sheath member 22 can be a single element, it is evident from the embodiment shown in FIGS. 1 and 2 that the sheath member 22 can include a plurality of sheaths, preferably a parallel pair of coaxially disposed sheaths, more particularly, a first, outer sheath 32 and a second, inner sheath 34. It is highly preferred that the first, outer sheath 32 be a locally and laterally flexible dilator sheath of the type disclosed in the parent patent application, incorporated by reference herein. (The sheath member 22, when present as only a single element, can also be the disclosed dilator sheath.)

As disclosed in more detail below with respect to the embodiment shown in FIG. 8, the snare 24 can be positioned about the sheath member 22. Alternatively, in the embodiment shown in FIGS. 1 and 2, the snare 24 can be positioned within the sheath member 22. More particularly, when the sheath member 22 comprises the first outer sheath 32 and the second inner sheath 34, it is highly advantageous that the snare 24 be coaxially positioned between distal ends 30 and 62 of outer sheath 32 and of inner sheath 34, respectively.

The snare 24 is preferably formed as a resilient but self-supporting metal coil 28 attached to the distal ends 30 and 62 of the outer sheath 32 and the inner sheath 34, respectively. The coil 28 includes a tag end 29 received in a transverse hole 31 through distal cutting tip 70 of the outer sheath 32, for attaching the coil 28 to the outer sheath 32. The coil 28 can of course be attached to the outer and inner sheaths 32 and 34 in any other convenient fashion.

Still with reference to FIGS. 1 and 2, the device 10 preferably also comprises a draw means 26 connected to the snare 24 and extending outwardly of the vascular system 18 of the patient 12, preferably outward of the patient 12. The draw means 26 preferably includes a proximal loop 27 acting as a graspable handle. The draw means 26 is moveable in a first, proximal direction, for example, by pulling on the proximal loop 27, so as to collapse the snare 24 about the encircled one of the proximal end 16 and distal end 20 of the elongated structure 14. In FIGS. 1 and 2, it is the distal end 20 that is encircled by the snare 24. It is highly preferred, however, that the draw means 26 is sufficiently rigid to also be moveable in the direction opposite to the first, proximal direction, so as to expand the snare 24 and free it from the encircled structure end 16 or 20. This permits the snare 24 to be disengaged from the elongated structure 14 and readily removed from the patient 12 should termination of the removal procedure be necessary, for example, in case ventricular arrhythmia or another complication develops.

Use of the device 10 to engage the distal end 20 of the elongated structure 14 and free the structure 14 of any encapsulating tissue may be aided by fixing the position of the structure 14 with respect to the patient 12. A locking stylet 56 can be engaged with the elongated structure 14 for this purpose. For example, locking stylets of the type disclosed in the second through seventh patent applications and patents cross-referenced above, and expressly incorporated by reference herein, are particularly useful as the locking stylet 56. The locking stylet 56 passes through the proximal end 16 of the elongated structure 14, and extends as far up the interior of the structure 14 as possible. This allows any coring cannula or sheath, such as a dilator sheath, to cut encapsulating tissue away from the elongated structure 14, rather than merely pushing the structure 14 and the encapsulating tissue more deeply into the patient 12. Introduction of the sheath member 22 into the patient 12 is facilitated by proximal end hub 60 or another positioning device external to the patient 12. Introduction of the sheath member 22 is also facilitated by the presence of a low-friction coating 66 over the sheath member 22, for example, over the first, outer sheath 32 if present, or over a dilator sheath.

Figure 3:
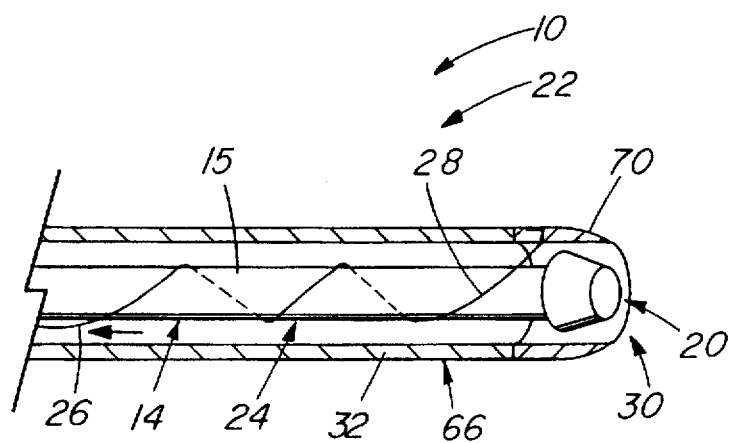
FIG. 3 is another cross-sectional view of a portion of the first preferred embodiment of the present invention during use.
Figure 4:
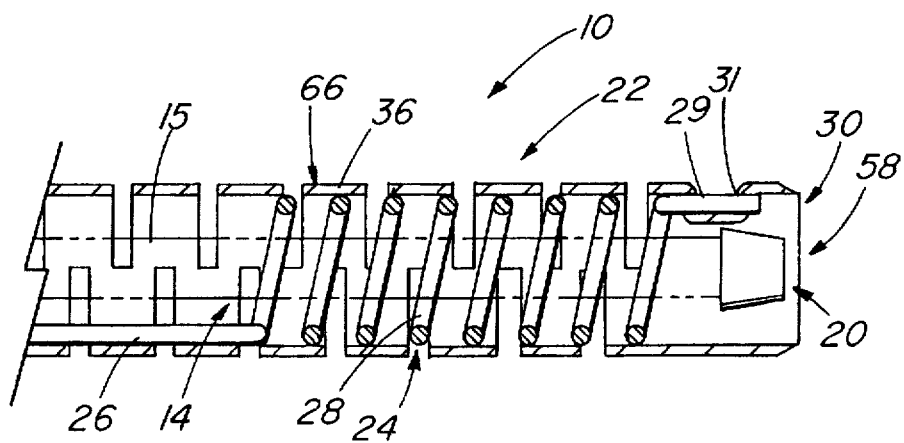
FIG. 4 is a cross-sectional view of another preferred embodiment of the present invention.

With reference now to FIG. 3, use of the embodiment of the device 10 shown in FIGS. 1 and 2 to remove or assist removal of the elongated structure can be readily understood. First, the locking stylet 56 is introduced into the elongated structure 14 as far as possible, through the proximal end 16 of the structure 14. The distal end 30 of the sheath member 22 is then positioned over the locking stylet 56 and the proximal end 16 of the elongated structure 14. The sheath member 22 is advanced along the structure 14 to separate or aid separation of any encapsulating tissue from the structure 14, and to move the snare 24 towards the distal end 20 of the elongated structure 14. Such separation is most easily achieved when the sheath member 22 comprises the locally and laterally flexible dilator sheath as depicted in FIG. 4, that is, when the sheath member 22 either is formed as, or includes as an element, the dilator sheath 36 of FIG. 4.

Preferably, once the distal end 30 of the sheath member 22 (and more particularly, the distal end 62 of the second, inner sheath 34) has passed over the distal end 20 of the elongated structure 14, the inner sheath 34 is preferably partially or completely withdrawn from at least the vascular system 18 of the patient 12, and preferably from the patient 12. This allows the coil 28 or other snare 24 to closely encircle the distal end 20 of the elongated structure 14. The draw means 26 is then moved in the direction shown by the arrow in FIG. 3, for example, by pulling on the proximal loop 27, which collapses the coil 27 onto the distal end 20 of the elongated structure 14. (Of course, the second, inner sheath 34 can alternatively be composed of a highly flexible material, and left in place while the draw means 26 is moved; the coil 28 would then be collapsed about both the inner sheath 34 and the distal end 20 of the elongated structure 14.) The elongated structure 14, now freed of any encapsulating tissue, can readily be removed from the patient 12 as desired, either by pulling on the sheath member 22, the draw means 26 and the locking stylet 56 all at the same time; or by pulling on only the draw means 26 and the locking stylet 56, leaving the sheath member 22 in place during removal of the structure 14.

Several alternative constructions for the snare 24 and sheath member 22 are equally useful in the practice of the present invention. For example, as shown in FIG. 4, the snare 24 can be compressively contained by the sheath member 22 or, in particular, locally and laterally flexible dilator sheath 36. More particularly, similar to the embodiment of FIGS. 1 and 2, the snare 24 is a coil 28, but the coil 28 of FIG. 4 possesses an uncompressed diameter greater than the inside diameter of the sheath member 22 (here, configured as the flexible dilator sheath 36). The coil 28 is radially compressed and inserted into the distal end 58 of the dilator sheath 36, and includes the tag end 29 for attachment to the dilator sheath 36. The coil 28 is sufficiently flexible to allow it to be drawn by the draw means 26 into the same type of shape disclosed in FIG. 3, and thereby engage the distal end 20 of the elongated structure 14. The coil 28 and dilator sheath 36, along with the engaged distal end 20 of the elongated structure 14, are then withdrawn together from at least the vascular system 18 of the patient 12, and preferably from the patient 12.

Figure 5:
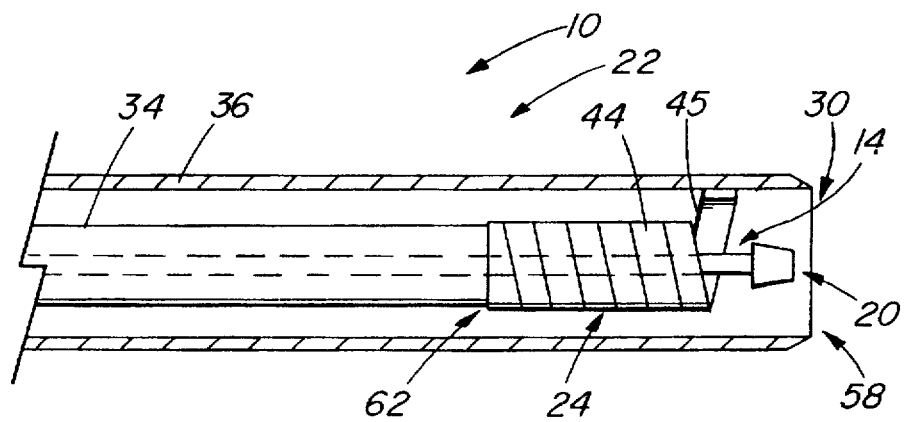
FIG. 5 is a cross-sectional view of another preferred embodiment of the present invention.

As shown in FIG. 5, the snare 24 need not be configured as a coil 28. Instead, the snare 24 can comprise a helically or cylindrically coiled leaf spring 44 connected to the distal ends 58 and 62 of the coaxial outer and inner sheaths 36 and 34. The coiled leaf spring 44 preferably includes a tag end 45 for affixing the spring 44 to the outer sheath 36. The spring 44 can readily be collapsed about the distal end 20 of the elongated structure by rotating the second, inner sheath 34 with respect to the outer, dilator sheath 36. The outer, dilator sheath 36 can be kept stationary during such rotation, or may be rotated in a contrary direction. In either case, the dilator and inner sheaths 36 and 34, as well as the engaged distal end 20 of the elongated structure 14, are withdrawn from the patient 12 together as a single unit.

Alternatively, as shown in FIG. 6, the snare 24 can be configured as a single wire loop 38 affixed to a draw means 26 contained in and extending through a thin metal tube 40. A synthetic cover sheath 41 is preferably positioned over the metal tube 40. In such a construction, the draw means 26 can merely be an extension of the loop 38 through the tube 40. The tube 40 includes a distal end 42 against which the loop 38 abuts, closing the loop 38 when the draw means 26 is moved in a direction outward of the patient 12. The wire loop 38 is preferably affixed to the sheath member 22 (particularly outer sheath 32 or dilator sheath 36) at its distal end 30. This affirmatively prevents withdrawal of the wire loop 38 into the tube 40 and ensures that the engagement of the wire loop 38 with the distal end 20 of the elongated structure 14 is reversible.

All of the previously disclosed embodiments of the device 10 of the present invention are particularly useful for engaging the distal end 20 of the elongated structure 14. However, as indicated above, the device 10 is also useful for engaging the proximal end 16 of the structure 14, and thereby serving either to remove the structure 14 from the patient, or to fix the position of the structure 14 with respect to the patient, and act as an extension over which a coring cannula or sheath (such as the outer sheath 32 or the dilator sheath 36) can be introduced.

The snare 24 previously described in relation to the embodiment of FIG. 6 is useful for this purpose. As shown in FIG. 7, however, when intended to engage the proximal end 16 rather than the distal end 20 of the elongated structure 14, the wire loop 38 is not affixed to the outer sheath 32 at all. The device 10 shown in FIG. 7 still includes the metal tube 40 and the cover sheath 41, but instead includes a pin 43 positioned across the distal end 42 of the tube 40, to prevent the wire loop 38 from being withdrawn into the tube 40. This ensures that the engagement of the wire loop 38 with the proximal end 16 of the elongated structure 14 is reversible. In this embodiment, the sheath member 22 can be considered as comprising the metal tube 40 and the outer sheath 32. However, dilator sheath 36 can also be readily used for outer sheath 32.

Use of the device 10 shown in FIG. 7 for fixing the position of the elongated structure 14 and as an extension for introduction of the dilator sheath is straightforward. The wire loop 38 is manually positioned about the proximal end 16 of the structure 14, and the draw means 26 moved outwardly of the patient 12, so as to collapse the wire loop 38 about the proximal end 16 of the structure 14. Such movement is most easily accomplished by pulling on the proximal loop 27. The distal end 30 of the outer sheath 32 is positioned over the tube 40, draw means 26, wire loop 38 and elongated structure 14, and the outer sheath 32 advanced along the structure 14 to separate it from any encapsulating tissue. The elongated structure 14 can then be removed from the patient 12 by pulling on the proximal loop 27 or the draw means 26. To further ease the insertion of sheath member 22 over tube 40 and proximal end 16 of the elongated structure 14, a proximally tapered outer sleeve 68 of, for example, a polymer material is positioned over the snared proximal end of the structure and the distal end of the tube 40.

Of course, the sheath member 22 need not be a coring cannula or sheath, and indeed need not be like the dilator sheath 36 at all, in order for it to deliver the snare 24 to the end 16 or 20 of the elongated structure. As shown in FIGS. 8 and 9, in contrast to the prior embodiments the snare 24 is positioned about the sheath member 22, rather than inside it. The snare 24 is configured as a cylindrical cage 46 formed from at least two, and preferably two, criss-crossed elongated loops 48 and 50. The loops 48 and 50 are advantageously composed of highly flexible wire, while the sheath member is composed of polytetrafluoroethylene or the like. An additional cover layer (not shown), such as a split piece of plastic tubing, can be positioned over the cage 46 to protect it from damage prior to use. The cage has a distal end 52 with a grasping means, such as a suture 54, attached to it. Draw means 26 and the proximal loop 27 are attached to the cage 46 opposite the distal end 52 of the cage 46.

Use of the device 10 of FIGS. 8 and 9 to fix the position of the elongated structure 14 with respect to the patient 12 can easily be understood. The distal end 30 of the sheath member 22 is introduced over the proximal end 16 of the elongated structure 14, and the device 10 slid onto the structure 14 until all of the cage 46 lies over the proximal end 16 of the structure 14. The sheath member 22 is then withdrawn from the elongated structure 14 in the direction of the arrow shown in FIG. 8, while the cage 46 is permitted to remain in position on the structure 14. The cage 46 can be preliminarily affixed to the elongated structure 14 by the suture 54; more conveniently, however, the suture 54 is merely grasped by a pair of forceps 64 while the draw means 26 is moved outward of the patient 12, in the direction of the arrow in FIG. 9. This collapses the cage 46 onto the proximal end 16 of the elongated structure 14, and the structure 14 will be fixed in position as long as the draw means is biased outwardly, for example, by pulling on the proximal loop 27. As in the embodiment shown in FIG. 7, if a coring cannula or sheath such as the dilator sheath 36 is then employed to separate the elongated structure 14 from any encapsulating tissue, pulling on the proximal loop 27 may be sufficient to remove the structure from the patient 12. Proximally tapered outer sleeve 68 is positioned over collapsed wire cage 46 and the proximal end 16 of the structure 14 to ease insertion of the dilator or outer sheath.

It is clear from the foregoing disclosure that the device 10 of the present invention is a remarkably versatile apparatus for removing, or for assisting in the removal of, a variety of elongated structures from a patient. The device 10 is believed to be most useful in removing cardiac leads such as pacemaker and defibrillator leads when it engages their distal ends. The device 10 is also useful for extending such leads and thereby allowing coring cannulae or sheaths to be inserted over them, while simultaneously fixing the position of such leads, thereby assisting removal of them.

The details of the construction or composition of the various elements of the disclosed embodiments of the device 10 are not believed to be critical to the achievement of the advantages of the present invention, so long as the elements possess the strength or flexibility needed for them to perform as disclosed. For example, the various sheaths may be composed of a physiologically compatible metal or organic material, and may be composites or combinations of these; for example, the outer and inner sheaths 32 and 34 of the sheath member 22 can comprise a polymeric tube with a metal grommet on its leading end. Furthermore, the outer and inner sheaths can be a transversely slotted metal tube as depicted by dilator sheath 36 in FIG. 4. The proximal loop 27 attached to the draw means 26 can be covered with shrink-wrap tubing, to make the draw means easier to manipulate. The draw means 26 itself may be formed continuously with the snare 24 or the proximal loop 27, or may be a separate wire or resilient rod connected to them. The snare 24 can be configured in any convenient shape, not merely in the shapes disclosed herein. The selection of these and other details of construction are believed to be well within the ability of one of even rudimentary skills in this area, in view of the present disclosure.

INDUSTRIAL APPLICABILITY

The present invention is useful in the performance of surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A device (10) for removing from a patient (12) a previously implanted elongated structure (14); the elongated structure (14) having an outside dimension, a proximal end (16), and a distal end (20) located within the patient; and the device (10) comprising in combination:

a sheath member (22) having an inside dimension greater than the outside dimension of the elongated structure (14); and a snare (24) associated with the sheath member (22) and shaped as a coil dimensioned to encircle one of the proximal end (16) and the distal end (20) of the elongated structure (14), the coil comprising a plurality of individual coil loops each dimensioned to encircle the one of the proximal end (16) and the distal end (20) of the elongated structure (14), and the sheath member (22) delivering the snare (24) to the one of the proximal end (16) and the distal end (20) of the elongated structure (14).

2. The device (10) according to claim 1, wherein the snare (24) is positioned about the sheath member (22).

3. The device (10) according to claim 1, wherein the snare (24) is positioned within the sheath member (22).

4. The device (10) according to claim 1, wherein the snare (24) is resilient but self-supporting.

5. The device (10) according to claim 4, wherein the sheath member (22) includes a distal end (30), and wherein the snare (24) is affixed to the distal end (30) of the sheath member (22).

6. The device (10) according to claim 1, wherein the snare (24) is a wire loop (38) and wherein the device (10) further comprises a tube (40) containing draw means (26) connected to the wire loop (38), the tube (40) having a distal end (42) abutting the wire loop (38).

7. The device (10) according to claim 1, further comprising a locking stylet (56) dimensioned to be received in the elongated structure (14) through the proximal end (16) of the elongated structure (14).

8. The device (10) according to claim 1, wherein the sheath member (22) comprises a dilator sheath (36).

9. The device (10) according to claim 1, further comprising draw means (26) connected to the snare (24) and extending outwardly of the patient (12), moveable in a first direction so as to collapse the snare (24) about the encircled one of the proximal end (16) and distal end (20) of the elongated structure (14).

10. The device (10) according to claim 9, wherein the draw means (26) is sufficiently rigid to expand the snare (24) when the draw means (26) is moved in a direction opposite to the first direction which collapses the snare (24).

11. A device (10) for removing from a patient (12) a previously implanted elongated structure (14); the elongated structure (14) having an outside dimension, a proximal end (16), and a distal end (20) located within the patient; and the device (10) comprising in combination;

a sheath member (22) having an inside dimension greater than the outside dimension of the elongated structure (14); and a snare (24) associated with the sheath member (22) and shaped as a coil dimensioned to encircle one of the proximal end (16) and the distal end (20) of the elongated structure (14), the sheath member (22) delivering the snare (24) to the one of the proximal end (16) and the distal end (20) of the elongated structure (14);

wherein the snare (24) is positioned within the sheath member (22), and wherein the snare (24) is compressively contained by the sheath member (22).

12. A device (10) for removing from a patient (12) a previously implanted elongated structure (14); the elongated structure (14) having an outside dimension, a proximal end (16), and a distal end (20) located within the patient; and the device (10) comprising in combination:

parallel first (32) and second (34) sheaths, at least one of the first (32) and second (34) sheaths having an axis, and at least one of the first (32) and second (34) sheaths having an inside dimension greater than the outside dimension of the elongated structure (14); and a snare (24) lying across the axis of, but positioned coaxially with, at least one of the first (32) and second (34) sheaths, the snare (24) being dimensioned to encircle one of the proximal end (16) and the distal end (20) of the elongated structure (14), and at least one of the first (32) and second (34) sheaths delivering the snare (24) to the one of the proximal end (16) and the distal end (20) of the elongated structure (14).

13. The device (10) according to claim 12, wherein the first (32) and second (34) sheaths are coaxial.

14. The device (10) according to claim 13, wherein the snare (24) is positioned between the first (32) and second (34) sheaths.

15. The device (10) according to claim 13, wherein the outermost of the first (32) and second (34) sheaths is a locally flexible dilator sheath (36).

16. The device (10) according to claim 12, further comprising a locking stylet (56) dimensioned to be received in the elongated structure (14) through the proximal end (16) of the elongated structure (14).

17. A device (10) for removing from a patient (12) a previously implanted elongated structure (14); the elongated structure (14) having an outside dimension, a proximal end (16), and a distal end (20) located within the patient; and the device (10) comprising in combination;

a sheath member (22) having an inside dimension greater than the outside dimension of the elongated structure (14): and a snare (24) associated with the sheath member (22) and dimensioned to encircle one of the proximal end (16) and the distal end (20) of the elongated structure (14), the sheath member (22) delivering the snare (24) to the one of the proximal end (16) and the distal end (20) of the elongated structure (14);

wherein the sheath member (22) comprises parallel first (32) and second (34) sheaths wherein the first (32) and second (34) sheaths are coaxial, and wherein the first (32) and second (34) sheaths each include a distal end (58 and 62), and the snare (24) is a coiled leaf spring (44) connected to and extending between the distal ends (58 and 62) of the first (32) and second (34) sheaths.

18. A device (10) for removing from a patient (12) a previously implanted elongated structure (14); the elongated structure (14) having an outside dimension, a proximal end (16), and a distal end (20) located within the patient; and the device (10) comprising in combination:

a sheath member (22) having an inside dimension greater than the outside dimension of the elongated structure (14); and a cylindrical cage (46) having a passage extending longitudinally therethrough formed from at least two crisscrossed elongated loops (48 and 50), associated with the sheath member (22) and dimensioned to encircle one of the proximal end (16) and the distal end (20) of the elongated structure (14), the longitudinal passage through the cylindrical cage (46) being dimensioned to encircle and receive therein the one of the proximal (16) and distal (20) ends of the structure (14) and the sheath member (22) delivering the cylindrical cage (46) to the one of the proximal end (16) and the distal end (20) of the elongated structure (14).

19. The device (10) according to claim 18, further comprising a locking stylet (56) dimensioned to be received in the elongated structure (14) through the proximal end (16) of the elongated structure (14).

20. A device (10) for removing from a patient (12) a previously implanted elongated structure (14); the elongated structure (14) having an outside dimension, a proximal end (16), and a distal end (20) located within the patient; and the device (10) comprising in combination;
- a sheath member (22) having an inside dimension greater than the outside dimension of the elongated structure (14); and
- a snare (24) associated with the sheath member (22) and dimensioned to encircle one of the proximal end (16) and the distal end (20) of the elongated structure (14), the sheath member (22) delivering the snare (24) to the one of the proximal end (16) and the distal end (20) of the elongated structure (14);
- wherein the snare (24) is a cylindrical cage (46) formed from at least two criss-crossed elongated loops (48 and 50), and wherein the cage (46) has a distal end (52), and wherein the device (10) further comprises a suture (54) for attaching the distal end (52) of the cage (46) to the elongated structure (14).

21. A device (10) for removing from a patient (12) a previously implanted elongated structure (14); the elongared structure (14) having an outside dimension, a priximal end (16), and a distal end (20) located within the patient; and the device (10) comprising in combination:
- a sheath member (22) having an inside dimension greater than the outside dimension of the elongated structure (14):
- a snare (24) associated with the sheath member (22) and dimensioned to encircle one of the proximal end (16) and the distal end (20) of the elongated structure (14), the sheath member (22) delivering the snare (24) to the one of the proximal end (16) and the distal end (20) of the elongated structure (14); and
- a locking stylet (56) dimensioned to be recieved in the elongated structure (14) through the proximal end (16) of the elongated structure (14).

22. A device (10) for removing from a patient (12) a previously implanted elongated structure (14); the elongated structure (14) having an outside dimension, a proximal end (16), and a distal end (20) located within the patient (12); and the device comprising in combination:
- a first, locally flexible dilator sheath (36) and a second sheath (34) coaxially contained in the first dilator sheath (36), the first dilator sheath (36) having a distal end (58), and the second sheath (34) having an inside dimension greater than the outside dimension of the elongated structure (14);
- a reversibly collapsible snare (24) positioned between the first dilator sheath (36) and the second sheath (34), the snare being dimensioned to encircle the distal end (20) of the elongated structure (14) and being shaped as a coil (28), affixed to the distal end (58) of the first dilator sheath (36);
- draw means (26) connected to the snare (24) and extending outwardly of the patient (12), for collapsing the snare (24) about the encircled distal end (20) of the elongated structure (14); and
- a locking stylet (56) dimensioned to be received in the elongated structure (14) through the proximal end (16) of the elongated structure (14).

* * * * *